United States Patent [19]

Betz

[11] Patent Number: 4,639,945
[45] Date of Patent: Feb. 3, 1987

[54] PROTECTIVE METHOD AND APPARATUS

[76] Inventor: John J. E. Betz, 423 Rose Garden Ct., Reno, Nev. 89509

[21] Appl. No.: 811,299

[22] Filed: Dec. 20, 1985

[51] Int. Cl.[4] .................. A41D 13/00; A61F 13/00
[52] U.S. Cl. ............................................ 2/22; 128/82
[58] Field of Search ........................ 2/59, 22; 128/82

[56] References Cited

U.S. PATENT DOCUMENTS

| | | | |
|---|---|---|---|
| 2,244,871 | 6/1941 | Guinzburg | 2/59 |
| 2,582,648 | 1/1952 | Mowbray | 128/505 |
| 4,178,924 | 12/1979 | Baxter | 128/82 |

Primary Examiner—Doris L. Troutman
Attorney, Agent, or Firm—Herbert C. Schulze

[57] ABSTRACT

This invention is a unique and improved shield to protect a limb which has been injured, is using an orthopedic device, bandage, or the like, or otherwise requires protection from water during bathing of patients or the like so concerned. The invention incorporates the use of a special sleeve to be slipped over a limb to be protected wherein the shield has an open end with a device suitable to encompass the limb and any bandage or other device associated with the limb and to allow easy engagement of the protective shield or sleeve, and wherein the device includes a flexible waterproof disk which will deform as necessary when being pulled over the limb and any appended involved. When fully in place, the flexible disk or the like seals about the shield and in combination with the sleeve or shield associated with it will protect the limb from any penetration of water.

10 Claims, 13 Drawing Figures

U.S. Patent  Feb. 3, 1987  Sheet 1 of 2  4,639,945
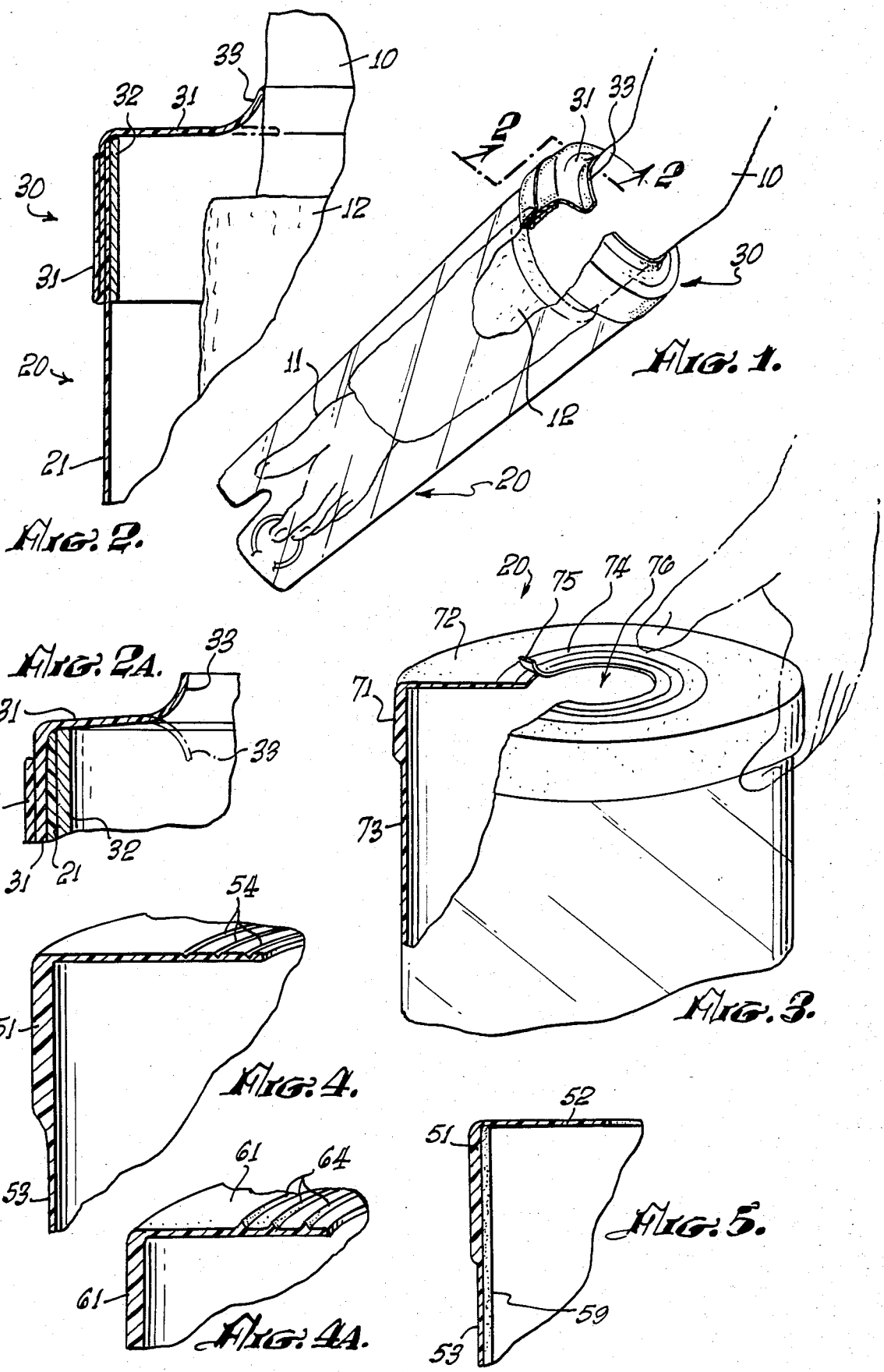

U.S. Patent  Feb. 3, 1987  Sheet 2 of 2  4,639,945
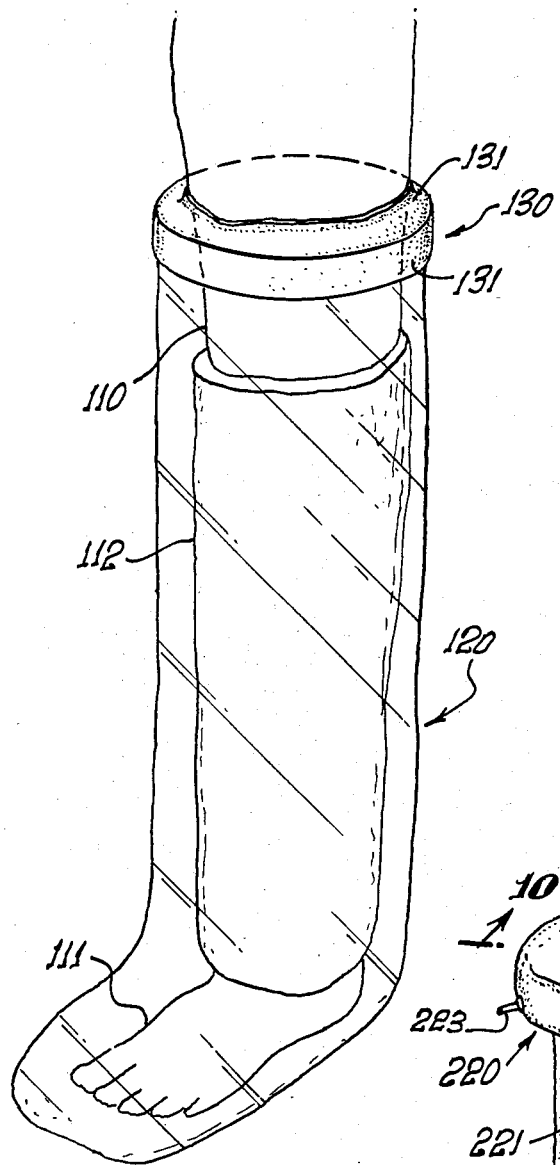
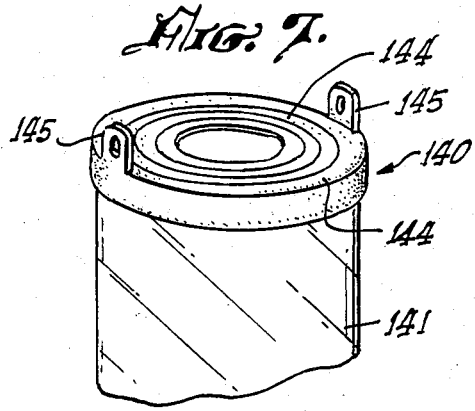
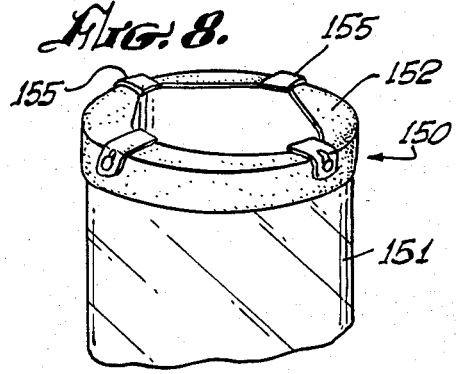
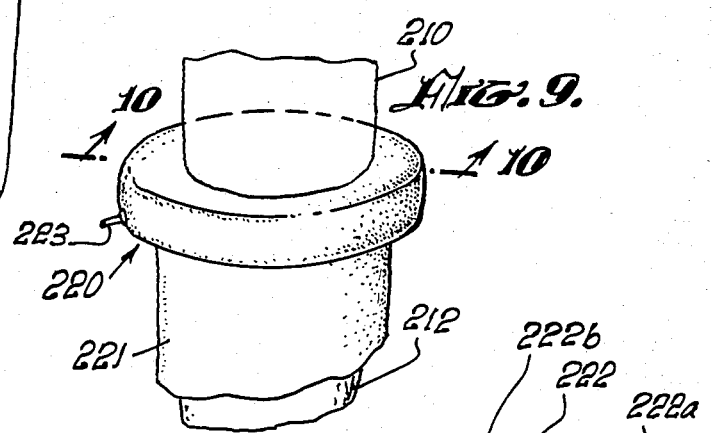
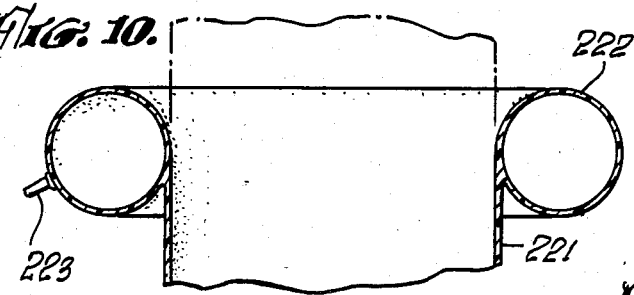
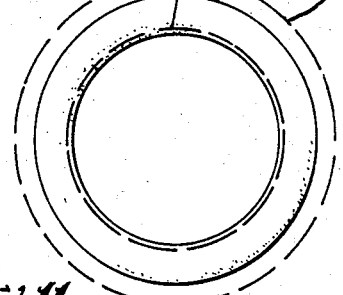

4,639,945

PROTECTIVE METHOD AND APPARATUS

CROSS REFERENCE TO RELATED PATENT APPLICATIONS

There are no applications related to this application filed by me.

BACKGROUND OF THE INVENTION

I. Field of the Invention

This invention is in the general field of protective devices for limbs, particularly those using orthopedic apparatus, other apparatus, bandages, and the like. The invention is more particularly directed to limbs using apparatus such as casts, bandages, and the to protect, sprained, or otherwise injured or infirm limbs. The method is even more particularly directed to the utilization of an apparatus utilizing a waterproof sleeve with a ring allowing for easy insertion over a limb, deformable so as to accommodate irregularities, and having in conjunction with the ring a gasket-like or sealing arrangement to seal around the limb and prevent the entry of moisture into the limb area.

II. Description of the Prior Art

There have been some elastic sleeves and the like developed for the same purpose as the method and apparatus of the present invention. These elastic sleeves and the like have numerous disadvantages, particularly in pressures which they apply upon the limb and because of the difficulty of applying them over a cast or the like on a limb.

To my knowledge, there has been no prior art wherein a gasket-like arrangement is utilized in conjunction with a loose fitting, oversized, waterproof protective device engaged with a deformable ring which allows for easy application over a limb having a cast, other problems, or the like.

SUMMARY OF THE INVENTION

Injuries to the limbs of humans (and animals) are wide spread and frequent. There are many ways of treating such injuries, but most commonly such injuries will require either a cast, a traction device, bandage, or some similar type well known treatment. Such treatments are effective and wide spread.

However, when a cast, bandage, or the like has been applied to a limb, it is usually necessary to keep the cast or the like and/or the limb dry, thus creating considerable problem in bathing the patient or under other circumstances where considerable moisture may be present.

As a result, patients using casts or the like or otherwise being treated frequently require an unusual amount of aid in bathing and in certain activities. This creates a loss of time and increased expense which is undesirable. Further, frequently the efforts of the best assistance may fail and a cast, bandage or the like may be ruined as the result of exposure to moisture and may require replacement. Such is generally not beneficial to the patient and can have serious adverse affects. Likewise, moisture penetrating the area may cause skin and other problems for the patient.

Some efforts have been made to provide waterproof coverings for casts and the like. Such efforts have primarily consisted of waterproof sheets which can be drawn over the cast and tightly encompass the limb immediately above the cast. Such is undesirable since circulation may be impaired and additionally it is quite difficult to draw such a device and remove it from a cast without causing discomfort to the patient or such that it must be removed and replaced, or it may cause a deformation of the healing limb. They don't actually seal.

I have studied this overall problem at length and have now conceived and developed a method, and apparatus for performing the method, by which a protective sheath around a cast or the like may be applied expeditiously and effectively with none of the disadvantages of the former devices. In accomplishing this I utilize a gasket-like arrangement to seal around the limb and a loose fitting waterproof sheath with a deformable application ring of sufficient dimensions to easily bring the sheath over the cast or other apparatus.

The gasket I use takes many configurations including, but not limited to, a disk-like gasket being deformable and having an opening therein such that it can encompass and seal the limb against moisture. Another form utilizes a pneumatic gasket which can be inflated so as to increase its diameter and deflated so as to decrease its diameter to cause a proper seal around the limb.

In practicing the method of this invention, a deformable ring is formed of such dimension that it will slip over the limb and any cast or the like being used as desired and may be deformed so as to accommodate varying cross sectional configurations of the cast or the like. The deformable ring is then properly affixed to a waterproof shield or sheath of sufficient dimension to totally encompass the cast or the like without presssure. Next, a gasket of sufficient configuration to seal, when desired, around the limb above the cast of the like is affixed to the deformable ring in such manner that the entire unit is impervious at its junctures to the ring and when applied the gasket causes an impervious seal about the limb.

It is an object of this invention to provide a waterproof shield for limbs which is easily applied and and seals about a limb;

Another object of this invention is to provide a method for applying such an apparatus in an economical manner to any form of apparatus being used to treat, or attached to a limb;

Another object of this invention is to provide such a method and apparatus as mentioned, wherein the sealing around a limb is accomplished by the use of a gasket.

Another object of this invention is to provide such a method and apparatus as mentioned, wherein the sealing around the limb is accomplished by a disk-like element which flexes and deforms so as to make a perfect seal about a limb;

Another object of this invention is to provide a pneumatically activated sealing ring.

The foregoing and other objects and advantages of this invention will become apparent to those skilled in the art upon reading the description of a preferred embodiment which follows in conjunction with a review of the appended drawings.

BRIEF DESCRIPTION OF THE DRAWINGS

FIG. 1 illustrates a human limb schematically and in perspective illustrating the use of aprotective device, to practice the method of this invention, partially broken away;

FIG. 2 is a section on 2—2 of FIG. 1;

FIG. 2A is a partially broken away partially sectioned view of the upper left area of FIG. 2;

FIG. 3 is a partially broken away partially sectioned schematic view of the device of FIG. 1 prior to being applied over a limb and showing a means for changing the size of the aperture in the top;

FIG. 4 is a partial view of an alternate embodiment of the apparatus of FIG. 3 illustrating only a limited portion thereof;

FIG. 4A shows in more detail certain of the important elements of the alternate embodiment of FIG. 4;

FIG. 5 illustrates in partial section another alternate construction to the upper portion of the device of FIGS. 1 and 3;

FIG. 6 illustrates still another embodiment of an apparatus to practice the method of this invention schematically and in perspective;

FIG. 7 is a broken away perspective of still another alternate embodiment of an apparatus similar to that of those shown in the foregoing figures;

FIG. 8 is a schematic perspective of the upper portion of a device used as in FIG. 6 illustrating another alternate embodiment;

FIG. 9 is a schematic perspective of a portion of the device utilizing an alternate embodiment of a sealing ring;

FIG. 10 is a section on 10—10 of FIG. 9; and

FIG. 11 is a top view on FIG. 9 illustrating the means of accomplishing sealing with this embodiment.

DESCRIPTION OF A PREFERRED EMBODIMENT

FIG. 1 shows a human limb (an arm) 10 with a hand 11, and a cast 12 intermediate the hand and the upper part of the arm.

A device generally 20 to practice the method of this invention is in place and comprises a sleeve generally 20 with an upper guide ring 30 incorporating a waterproof material 31 having its upper portion in the form of a more or less flat disk with a deformable edge 33 about an opening which accommodates the arm 10. FIG. 2 shows in somewhat detail the arm 10, the cast 12, the sleeve 21 (generally 20) and the supporting ring arrangement 31 and 32 which form a relatively rigid ring around the upper part of the sleeve 21. The various layers of material will be fastened together with adhesive or by electronic welding or the like as is known to those skilled in the art.

The upper portion of the element 31 is shown in somewhat more detail in FIG. 2A, particularly with its operation as it may be drawn on to the limb. When being drawn onto the limb, the lip 33 may bend downward as shown in the phantom position. However, when fully in place, this lip will then snap up into the position shown in FIG. 2 and FIG. 2A in its non phantom view and will thus create a seal around the limb wherein water or the like can drain down about this smoothly conforming lip.

As shown at FIG. 3, a device such as that shown in FIGS. 1, 2, and 2A, can be made wherein the element 73 serves the use of element 21 above described and the element 72 will be serving the purpose of the area 31. At 71, the extra thickness will create a ring structure which is easy to grasp as shown and to pull on against some pressure if necessary.

By having a series of scored areas as indicated, the opening 76 can be enlarged by removing individual strips along this scored area such as the strip 75 shown in FIG. 3 as being partially removed.

In FIG. 4, a structure similar to that shown in FIG. 3 is shown in slightly more detail where it is shown that there are grooves at 54 which are a part of a disk-like portion of the element 51. In this case the entire element is formed of one material wherein there is a thinner sleeve 53, and an enlarged and stiffened portion 51, and the upper flat area with the grooves at 54 which allow for making an opening suitable for the particular use desired.

FIG. 4A shows a similar structure, but wherein the markings for tear away sections to open the opening to a larger position are indicated as ridges 64 and will be used as guides to be cut with a knife or the like. Thus the upper disks 61 can be caused to have an opening of whatever size may be desired.

In FIG. 5 there is shown a structure similar to the prior structures with a sleeve 53, an upper enlarged and strengthened area 51, and the disk top 52, In this case there has been added a lining 59 which will contain a desiccant or otherwise be suitable to absorb any moisture which might by chance get inside the sleeve.

In FIG. 1 a loop is shown adjacent the fingers of the individual involved on the interior of the sleeve. By use of this type arrangement, the user of the item can pull upward on the ring and assist in its proper use.

FIG. 6 illustrates a foot 111 on leg 110 with a cast 112. In this case the sleeve 120 has been made with an enlarged area at the bottom to accommodate the general shape of the foot. This is not necessary but may be desired in some instances. The structure at 130 and 131 will be similar to that shown in the prior illustrations and will be understood by those skilled in the art.

FIG. 7 shows a sleeve 141 with the reinforced ring portion 140 and the flat top 144. There has been added to this a pair of ears 145 which can be used to assist in pulling the device into place. The ears, having holes in them, can be easily utilizied and even used to fasten over a shoulder or the like to hold the device in place.

FIG. 8 illustrates another alternate embodiment in which the sleeve 151 with the strengthened ring area 150 has its flat top 152 pulled open by a series of straps 155 which are fastened by means known to those skilled in the art in such manner as to have a large opening. Once the device is in place, the straps 155 may be relieved and a seal will be accomplished around the limb.

At FIG. 9 there is shown a sleeve 221 about a leg 210 having a cast 212. The sleeve 221 is attached to a sealing ring 220, which is a hollow doughnut shaped ring of rubber or other suitable resilient material. It has a valve 223 attached as indicated.

In FIG. 10 it can be seen that the sleeve 221 is either adhered to or formed integrally with the hollow ring 222 and the valve 223 intersects into the interior of the ring 222.

In FIG. 11 it will be shown that the ring 222 will have the ability to deform in a manner known to those skilled in the art when air or the like is injected into the valve 223. Thus the interior dimension as shown at 222B will move outwardly from the limb itself depending upon the exact construction materials, which is known to those skilled in the art.

The outer perimeter of the ring 222 will also move as indicated at 222A. Thus, the ring may be inflated so that it can slip over the cast as well as the limb or anything else which may be involved and then air can be let out of the ring until an appropriate pressure is achieved against the limb to avoid the entrance of moisture.

In using the device of the last described category, the sleeve will be slipped up over the limb when the ring is in a well inflated position so that it clears the limb and all protrusions. The ring itself can be used as a handle or guide means. When it is in place, the ring will be deflated until a proper seal is achieved around the limb.

While the embodiments of this invention shown and described are fully capable of achieving the objects and advantages desired, it is to be understood that such embodiments have been shown for purpose of illustration only, and not for purposes of limitation.

I claim:

1. The method of protecting a limb from undesired moisture comprising forming a waterproof sleeve open at one end and closed at its other end suitable to encompass the limb desired to be protected from moisture; forming at the open end of the sleeve a reinforced area comprising a semi-rigid formable ring attached to the said sleeve; forming a relatively flat disk across the top of the semi-rigid formable ring said disk having a size adjustable opening therein suitable to be drawn over a limb; drawing the said device over the limb in such manner that the inner opening of the disk forms a waterproof seal about the limb.

2. The method of claim 1 wherein means are provided to assist in pulling said device over a limb, which means comprise handle means.

3. The method of claim 1 wherein prior to placing the device over the limb a portion of the disk is removed so as to create an appropriate size to receive the limb.

4. Apparatus for protecting a limb from moisture comprising a sleeve of resilient waterproof material closed at one end and open at the other end; a deformable, semi-rigid waterproof ring attached to the open end of said sleeve; a disk attached to the said deformable ring at a 90 degree relationship to the length of the sleeve, said disk having a size adjustable opening in its center suitable to encompass the circumference of a limb.

5. The apparatus of claim 4 wherein the opening in said disk is provided with means for uniformly and adjustably enlarging said opening in its center by successive removal of predetermined circular strips of disk material.

6. The apparatus of claim 5 wherein the said ring, disk, and sleeve are integrally formed as one piece.

7. The apparatus of claim 6 wherein means are connected to connected to said ring for purposes of pulling it over a limb.

8. The apparatus of claim 7 wherein said means to pull the sleeve over the limb are provided with means to fasten the entire sleeve in position upon the limb.

9. The apparatus of claim 7 wherein means are provided to temporarily enlarge the opening in said disk until the apparatus is in place upon a limb.

10. An apparatus for protecting a limb of a human being from moisture, comprising in combination: a sleeve of resilient waterproof material closed at one end and open at the other end, of such size as to totally encompass a predetermined desirable area of said limb; a deformable, semi-rigid, waterproof ring attached to the open end of said sleeve; a disk, comprising a series of detachable circular elements, each being composed of waterproof material, attached to the edge of said deformable ring farthest from the opposed end of said sleeve at a 90 degree relationship to the length of the sleeve, said disk having an adjustable opening in its center suitable to encompass the circumference of a limb, which adjustment comprising a series of circular premarked rings which can be removed one ring at a time to increase the size of the opening to accommodate the appropriate circumference of the limb to which the device is applied.

* * * * *